United States Patent
Calame et al.

(10) Patent No.: US 6,360,598 B1
(45) Date of Patent: Mar. 26, 2002

(54) BIOMECHANICAL MEASURING ARRANGEMENT

(75) Inventors: Christian Calame, Winterthur; Hans Conrad Sonderegger, Neftenbach, both of (CH)

(73) Assignee: K.K. Holding AG, Winterthur (SE)

( * ) Notice: Subject to any disclaimer, the term of this patent is extended or adjusted under 35 U.S.C. 154(b) by 0 days.

(21) Appl. No.: 09/661,642

(22) Filed: Sep. 13, 2000

(30) Foreign Application Priority Data

Sep. 14, 1999 (CH) ................................. 1679/99

(51) Int. Cl.$^7$ ................................................ A61B 5/00
(52) U.S. Cl. ..................... 73/172; 73/862.046
(58) Field of Search .............................. 73/172, 862.41, 73/862.042, 862.043, 862.044, 862.045, 862.046

(56) References Cited

U.S. PATENT DOCUMENTS

| | | | |
|---|---|---|---|
| 3,504,540 A | | 4/1970 | Pradko et al. |
| 3,894,437 A | | 7/1975 | Hagy et al. |
| 4,050,532 A | * | 9/1977 | Provi et al. ................. 177/211 |
| 4,136,682 A | | 1/1979 | Pedotti |
| 4,703,663 A | * | 11/1987 | Oppermann ............. 73/862.68 |
| 4,739,848 A | * | 4/1988 | Tulloch ....................... 177/211 |
| 4,928,959 A | | 5/1990 | Bassett et al. |
| 5,029,483 A | | 7/1991 | Gautschi et al. |
| 5,083,467 A | * | 1/1992 | Tabota ..................... 73/826.04 |
| 5,186,062 A | | 2/1993 | Roost |
| 5,299,454 A | | 4/1994 | Fuglewicz et al. |
| 5,449,864 A | * | 9/1995 | Beatty et al. ............. 177/25.14 |
| 5,469,740 A | | 11/1995 | French et al. |
| 5,574,669 A | | 11/1996 | Marshall |
| 5,714,694 A | * | 2/1998 | Diessner ................ 73/862.632 |
| 5,913,242 A | | 6/1999 | Stüssi |

* cited by examiner

*Primary Examiner*—Max Noori
(74) *Attorney, Agent, or Firm*—Barnes & Thornburg

(57) ABSTRACT

For more accurate analysis of the motions of human beings and animals, two commercial measuring systems, namely a force measuring platform fitted with piezoelectric crystal sensors and a high-resolution surface pressure distribution measuring system equipped with a large number of vertical force sensors, are combined and preferentially joined by gluing to form a single measuring unit.

9 Claims, 1 Drawing Sheet

BIOMECHANICAL MEASURING ARRANGEMENT

BACKGROUND AND SUMMARY OF THE INVENTION

The invention concerns a biomechanical measuring arrangement for simultaneously detecting the total force distribution and and pressure distribution over the surface for analyzing the motions of human beings and animals.

For such analyses, both force measuring platforms and mats for measuring the pressure distribution over the surface are known. Already published also is a combination of pressure distribution measuring plate fitted with polymer sensors of small size with piezoelectric sensors, not described in detail, under the designation "hybrid plate". This combination is said to make possible continuous calibration of the pressure distribution measuring plate.

With these devices, an exact detection of the total force by magnitude and direction of the motions of human beings and animals, and at the same time of the pressure distribution over the surface, is not possible. Here the invention provides remedy by combining a commercial force measuring platform fitted with piezoelectric crystal sensors and a likewise commercial high-resolution pressure distribution measuring system having a large number of vertical force sensors spaced over the surface without gaps, and a signal processing unit which processes and displays the signals from both measuring systems. The processing and recording of the signals from both measuring systems can be accomplished very advantageously, separately and independently of each other, in a circuit without delay.

The combination of the two measuring systems makes possible new insights into the motion sequence and pressure distribution patterns. In particular the spatial analysis of the total force vector with the planar pressure distribution provides interesting evaluation possibilities. Knowledge of the third dimension gives the detailed data from the pressure distribution measuring system much greater information value, allowing overall monitoring of its many individual forces.

The control data of the force measuring platform are therefore crucially important, because they can be detected much more accurately than the numerous individual forces of the pressure distribution measuring system, of which the measured values can be obtained only by relatively inaccurate methods.

The combination of a large number of relatively inaccurate sensors with the very accurate piezoelectric measuring platform—especially the detection of the shear forces acting in the surface by using multicomponent sensors in the platform—enables new information to be gathered on the motions of human beings and animals.

From suitable combinations of the signals from the platform and those from the pressure distribution measuring system, a number of software packages can be evolved, tailored to specific questions and applications.

Other objects, advantages and novel features of the present invention will become apparent from the following detailed description of the invention when considered in conjunction with the accompanying drawings.

DETAILED DESCRIPTION OF THE PREFERRED EMBODIMENTS

Figure 1:
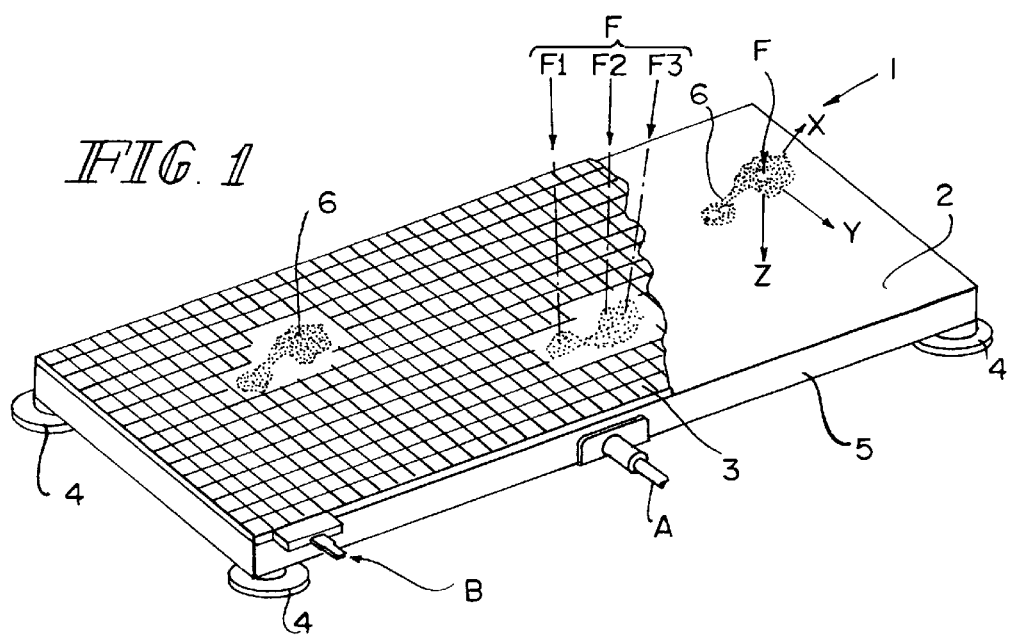
FIG. 1 shows a typical embodiment for the biomechanical measuring arrangement according to the invention.

The known force measuring platform 1 (FIG. 1) consists of a rectangular base plate 5, supported at its corners on the ground through four supports 4 fitted with crystal sensors not shown. Located on its surface is a likewise known pressure distribution measuring system 3, here in the form of a flexible mat, and joined to the base plate 5 by gluing to form one unit. The pressure distribution managing system may be smaller than the force measuring platform although they are shown as coextensive.

The high-resolution mat for measuring the pressure distribution consists for example of a large number of relatively small vertical polymer force sensors measuring typically a few square millimetres ($mm^2$), whose measuring signals are led via a signal output B to a signal processing unit not shown. This consists advantageously of an electronic data processing facility programmed for a given application. If necessary, the mat may be replaced by a relatively fixed plate.

The piezoelectric crystal sensors in the supports 4 consist advantageously of quartz. These sensors may be either single-component sensors for individual measurement of the vertical force component $Fz$, or multicomponent sensors detecting the shear force components $Fx$ and $Fy$ acting along in the surface as well as the vertical component $Fz$. To illustrate this, in zone 2 of the platform 1 part of the pressure distribution measuring system 3 has been left out. In its place is a rectangular coordinate system for the components $Fx$, $Fy$ and $Fz$ of the footprint 6 loaded with the total force F. The force measuring platform or base plate 5 may be divided length wise for detecting the total force of each of the left and right foot.

The force measurement signals pass via a signal output A likewise to the data processing facility mentioned. In this, both measuring signals may be processed and displayed advantageously, separately and independently of each other and without delay. Of course it is also possible to overlay the signals from both systems if necessary.

In FIG. 1 two additional footprints one left and one right foot, are shown in the zone of the mat 3. Three components F1, F2 and F3 of the total force vector F are indicated for the right foot. The force measuring platform or base plate 5 may be divided lengthwise for detecting the total force for each of the right and left foot.

Figure 2:
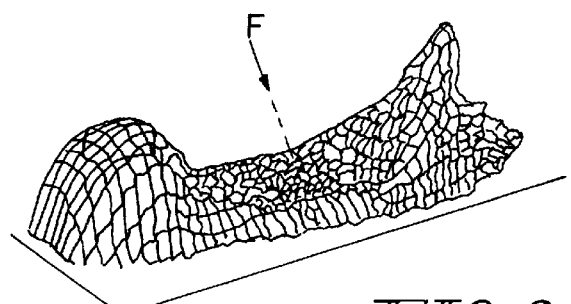
FIG. 2 shows a three-dimensional diagram of a footprint plotted with the pressure distribution measuring system.
Figure 3:
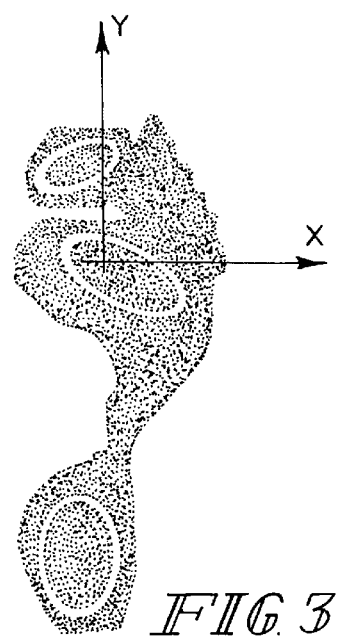
FIG. 3 shows the various pressure zones under a footprint, again plotted by the pressure distribution measuring system.

FIGS. 2 and 3 show two different possibilities for presenting a processing of the segments of the pressure distribution system 3. FIG. 2 shows the distribution under a footprint 6 as a familiar three-dimensional "mountain". FIG. 3 shows it as a contoured two-dimensional "map" in which the different pressure areas may be shown in different colors.

Figure 4:
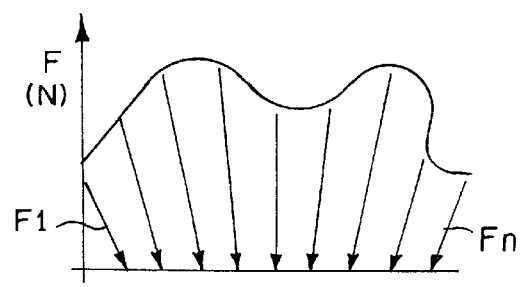
FIG. 4 finally shows a spatial force vector diagram for the total force vector recorded with the force measuring platform.

Finally FIG. 4 gives a familiar plot of the total force vector F resolved into its individual components F1 to Fn. The horizontal axis represents the time t, and the vertical axis the force in newtons (N).

The evaluation of the two simultaneously impacted but independent measuring systems is governed by the particular application and is laid down advantageously in the software for the data processing facility, but this will not be enlarged upon here. Although the present invention has been described and illustrated in detail, it is to be clearly understook that the same is by way of illustration and example only, and is not to be taken by way of limitation. The spirit and scope of the present invention are to be limited only by the terms of the appended claims.

What is claimed is:

1. A biomechanical measuring arrangement for simultaneously detecting the total force distribution and the pressure distribution over a surface, for analyzing motions of human beings and animals, the arrangement comprising acombination of a force measuring platform equipped with piezoelectric crystal sensors, and a high-resolution pressure distribution measuring system having a large number of vertical force sensors spaced over a surface without gaps, and a signal processing unit processing and displaying the signals from both measuring systems.

2. The biomechanical measuring arrangement according to claim 1, wherein the signal processing unit processes and displays separately and independently of each other the signals from both measuring systems in a circuit without delay.

3. The biomechanical measuring arrangement according to claim 1, wherein the force measuring platform includes multicomponent sensors.

4. The biomechanical measuring arrangement according to claim 1, wherein the force measuring platform is divided lengthwise for detecting the total force of end of a left and right foot.

5. The biomechanical measuring arrangement according to claim 1, wherein the two measuring systems are coextensive.

6. The biomechanical measuring arrangement according to claim 1, wherein the pressure distribution measuring system is smaller than the force measuring platform.

7. The biomechanical measuring arrangement according to claim 1, wherein the two measuring systems are joined together by gluing.

8. The biomechanical measuring arrangement according to claim 1, wherein the pressure distribution measuring system is a flexible mat.

9. The biomechanical measuring arrangement according to claim 1, wherein the pressure distribution measuring system is a fixed plate.

* * * * *